United States Patent
Segui et al.

(10) Patent No.: US 10,144,772 B2
(45) Date of Patent: Dec. 4, 2018

(54) METHOD FOR TREATING MELANOMA

(71) Applicants: INSERM (INSTITUT NATIONAL DE LA SANTÉ ET DE LA RECHERCHE MÉDICALE), Paris (FR); CENTRE HOSPITALIER UNIVERSITAIRE DE TOULOUSE, Toulouse (FR); INSTITUT CLAUDIUS REGAUD, Toulouse (FR); UNIVERSITÉ PAULS SABATIER TOULOUSE III, Toulouse (FR)

(72) Inventors: Bruno Segui, Toulouse (FR); Nathalie Andrieu-Abadie, Toulouse (FR); Thierry Levade, Toulouse (FR); Celine Colacios Viatge, Toulouse (FR); Philippe Rochaix, Toulouse (FR); Florie Bertrand, Toulouse (FR); Herve Benoist, Toulouse (FR); Julia Rochotte, Toulouse (FR)

(73) Assignees: INSERM (Institut National de la Sante et de la Recherche Medicale), Paris (FR); Centre Hospitalier Universitaire de Toulouse, Toulouse (FR); Institut Claudius Regaud, Toulouse (FR); Universite Paul Sabatier Toulouse III, Toulouse (FR)

( * ) Notice: Subject to any disclaimer, the term of this patent is extended or adjusted under 35 U.S.C. 154(b) by 0 days.

(21) Appl. No.: 15/310,158

(22) PCT Filed: May 12, 2015

(86) PCT No.: PCT/EP2015/060512
§ 371 (c)(1),
(2) Date: Nov. 10, 2016

(87) PCT Pub. No.: WO2015/173259
PCT Pub. Date: Nov. 19, 2015

(65) Prior Publication Data
US 2017/0174744 A1    Jun. 22, 2017

(30) Foreign Application Priority Data

May 12, 2014  (EP) .................................. 14305687

(51) Int. Cl.
| | |
|---|---|
| *A61K 38/17* | (2006.01) |
| *A61K 39/00* | (2006.01) |
| *C07K 16/24* | (2006.01) |
| *C07K 16/28* | (2006.01) |
| *C07K 16/30* | (2006.01) |
| *C07K 14/715* | (2006.01) |
| *G01N 33/574* | (2006.01) |

(52) U.S. Cl.
CPC ...... *C07K 14/7151* (2013.01); *A61K 38/1793* (2013.01); *C07K 16/241* (2013.01); *C07K 16/2878* (2013.01); *C07K 16/3053* (2013.01); *G01N 33/5743* (2013.01); *A61K 2039/505* (2013.01); *A61K 2039/55* (2013.01); *C07K 2317/21* (2013.01); *C07K 2317/24* (2013.01); *C07K 2317/76* (2013.01); *C07K 2319/30* (2013.01); *G01N 2333/525* (2013.01); *G01N 2333/70539* (2013.01)

(58) Field of Classification Search
None
See application file for complete search history.

(56) References Cited

PUBLICATIONS

Sasi et al. Breaking the 'harmony' of TNF-a signaling for cancer treatment. Oncogene, 31, 4117-4127, 2012.*
Palmiere G et al: "TNFimpairs in vivo and in vitro natural killer (NK) susceptibility of B16 melanoma cells.", Scandinavian Journal of Immunology Mar. 1992, Mar. 1992, vol. 34, No. 3, pp. 279-287.
S. J. Roberts et al: "Characterizing tumor-promoting T cells in chemically induced cutaneous carcinogenesis" Proceedings of The National Academy of Sciences, Apr. 17, 2007, vol. 104, No. 16, pp. 6770-6775.
U. S. Wilmott et al: "Dynamics of Chemokine, Cytokine, and Growth Factor Serum Levels in BRAF-Mutant Melanoma Patients during BRAF Inhibitor Treatment", The Journal of Immunology, Jan. 31, 2014, vol. 192, No. 5, pp. 2505-2513.
Bergenwald C et al: "Variable expression of tumor necrosis factor alpha in human malignant melanoma localized by in situ hybridization for mRNA.", Cancer Immunology, Immunotherapy : CII Aug. 1997, Aug. 1997, vol. 44, No. 6, pp. 335-340.
Mroweitz U et al: The chemokine RANTES is secreted by human melanoma cells and is associated with enhanced tumour formation in nude mice:, British Journal of Cancer 1999 GB, 1999, vol. 79, No. 7-8, pp. 1025-1031.
Trentin L et al: "Tumour-infiltrating lymphocytes bear the 75 kDa tumour necrosis factor receptor", British Journal of Science, 1995, vol. 71, No. 2, pp. 240-245.

* cited by examiner

*Primary Examiner* — Elly-Gerald Stoica
(74) *Attorney, Agent, or Firm* — W&C IP (57) ABSTRACT

The present invention relates to a TNFα blocking agent for use in the treatment and prevention of melanoma in a subject in whom melanoma cells express MHCI and in whom stroma cells exhibit TNF expression.

12 Claims, 5 Drawing Sheets

Figure 1 A, B and C

Figure 1D

Figure 2 A and B

Figure 3 A, B, and C

Figure 4

METHOD FOR TREATING MELANOMA

FIELD OF THE INVENTION

The present invention relates to a TNFα blocking agent for use in the treatment and prevention of melanoma in a subject in whom melanoma cells express MHCI and in whom stroma cells exhibit TNFα expression.

BACKGROUND OF THE INVENTION

Tumor Necrosis Factor α (TNF-α) is a major inflammatory cytokine, which has been initially identified in 1975 for its ability to trigger necrosis of cutaneous mouse fibrosarcoma in vivo. At variance with prior knowledge, a growing body of evidence in mouse models indicates that TNF produced by cancer and/or stromal cells may favour the establishment of a pro-inflammatory microenvironment, modulating specific anti-cancer immune response and enhancing tumor angiogenesis, tumor progression and metastasis.

Different studies have illustrated the role of TNF in skin tumor formation. As compared to their wild-type counterparts, TNF-deficient mice, TNF-R1-deficient mice and, albeit to a lesser extent, TNF-R2-deficient mice are reluctant to carcinogen-induced benign skin tumor (i.e., papillomas) formation. However, malignant progression from skin papilloma to carcinoma is similar in wild-type and TNF-deficient mice. The conclusion was that TNF plays an important role in the early stages of tumor promotion, most likely through its ability to trigger local inflammation. Indeed, the characterization of TNF-deficient mouse skin indicates an increased CD8 T cell infiltration upon DMBA/TPA treatment as compared to their wild-type counterparts.

The role of TNF in melanoma remains controversial. Injection of high levels of recombinant TNF triggers necrosis of melanoma, not only in mice, but also in humans and is currently used in isolated limb perfusion in the clinic (Balkwill F. 2009). The pro-necrotic TNF effect is likely dependent on its ability to induce apoptosis of endothelial cells. In sharp contrast, it has been recently shown that TNF, which is produced in patients treated with BRAF V600E inhibitors (Wilmott et al, 2014), may confer resistance of human melanoma by increasing Twist1 levels (Menon, D. R. et al 2013). The role of TNF in melanoma has been further investigated in mice using B16 melanoma cells, which do not express TNF endogenously. Whereas ectopic membrane TNF on B16 cells triggers TNF-R2-dependent pro-tumoral myeloid cell death, and subsequent impaired in vivo melanoma growth, ectopic expression of soluble TNF at low levels by B16 has opposite effect on melanoma growth in mice, most likely through its ability to enhance tumor angiogenesis (Li, B. et al, 2009). Both B16 cell growth and tumor angiogenesis are reduced in TNF-R2-deficient mice. Moreover, lung invasion of intravenously injected B16 melanoma cells is decreased in TNF-/- and TNF-R2-/- mice, indicating that TNF likely enhances melanoma dissemination in a TNF-R2-dependent manner (Chopra, M. et al, 2013). Vaccination towards TNF triggers self anti-TNF antibodies and inhibits lung invasion of intravenously injected B16 melanoma cells. Similar data have been obtained by injecting anti-TNF neutralizing antibodies or soluble TNF-R1, indicating that TNF blockade may represent an interesting strategy to prevent melanoma metastasis. A recent study showed that TNF deficiency can delay tumor growth in a spontaneous mouse model of BRAF V600E melanoma (Smith M P et al., 2014) In humans, different case reports have documented the occurrence of melanoma in patients with autoimmune disorders treated with anti-TNF. However, recent meta-analyses do not confirm the association of anti-TNF treatments and an increased melanoma incidence.

TNF is involved in the modulation of both innate and specific immune responses. Whereas TNF is produced by Natural Killers (NK), it reduces the susceptibility of B16 melanoma cells to NK cells, at least in part, by enhancing MHC class I expression at the cell surface of melanoma cells (Palmieri G et al, 1992). Conflicting results have been published on the role of TNF in the CD8 T cell immune response towards cancer cells. On the one hand, TNF acts as an effector molecule in CD8 T cell-triggered cell death of cancer cells and a co-stimulatory cytokine able to enhance naive CD8 T cell proliferation and cytokine secretion. In addition, TNF is required for the establishment of anti-tumor immune response by facilitating dendritic cell maturation as well as CD8 T cell activation and tumor infiltration. On the other hand, TNF triggers TNFR2-dependent activation-induced cell death (AICD) in CD8 T cells, thus likely limiting immune response duration. Moreover, TNF may behave as an immunosuppressive cytokine, facilitating the increased number of regulatory T and B cells as well as Myeloid-Derived Suppressor Cells (MDSC). In an adoptive transfer therapy protocol of specific CD8 T cells in mice, TNF could induce dedifferentiation of melanoma cells associated with a decrease of melanocytic antigen expression, likely contributing to tumor relapse. The latter study indicates that TNF putatively contributes to melanoma immune escape.

Recently, some tumor blood vessels, designated tumor high endothelial venules (HEVs), which mediate lymphocyte entry, have been found in human breast and melanoma (Martinet, L., 2012) tumors. HEVs display cuboidal morphology and express high levels of sulfated carbohydrate ligands for L-selectin (CD62L), which mediates lymphocyte rolling along endothelium. In humans, the density of HEVs (denoted as MECA79+ vessels) is highly correlated with CD8 T cell tumor infiltration and inflammation as evaluated by an increased expression of pro-inflammatory cytokines. In this context, the TNF expression level and its putative role in CD8 T cell melanoma infiltration and HEV differentiation have not been investigated.

SUMMARY OF THE INVENTION

The inventors evaluated TNF role in CD8 T cell-dependent immunity in experimental melanoma. Their data indicate that (i) TNF was robustly expressed by stromal cells from human primary melanoma, exhibiting high CD8 T cell infiltration and HEV density; (ii) TNF was unlikely instrumental for both events but rather may constitute a negative feedback for CD8 T cell-dependent anti-melanoma immune response in B16 mouse melanoma, which constitutively express MHCI at high levels; (iii) anti-TNF enhanced CD8 T cell-dependent immune response, thus limiting immunogenic B16 melanoma growth in mice.

The present invention relates to a TNFα blocking agent for use in the treatment and prevention of melanoma in a subject in whom melanoma cells express MHCI and in whom stroma cells exhibit TNFα expression.

DETAILED DESCRIPTION OF THE INVENTION

A first object of the invention relates to a TNFα blocking agent for use in the treatment and prevention of melanoma in a subject in whom melanoma cells express MHCI and in whom stroma cells exhibit TNFα expression.

As used herein, the term "MHCI" for Major Histocompatibility Complex of class I denotes is one of two primary classes of major histocompatibility complex (MHC) molecules (the other being MHC class II) and are found on nearly every nucleated cell of the body. Its function is to display fragments of proteins from within the cell to T cells; healthy cells will be ignored, while cells containing foreign or mutated proteins will be attacked by the immune system. Because MHC class I molecules present peptides derived from cytosolic proteins, the pathway of MHC class I presentation is often called the cytosolic or endogenous pathway.

As used herein, the term "treatment and prevention of melanoma in a subject in whom melanoma cells express MHCI", denotes a subject with melanoma cells, which express MHC Class I protein, as evaluated by flow cytometry, immunohistochemistry or western blot.

As used herein, the term "treatment and prevention of melanoma in a subject in whom stroma cells exhibit TNFα expression" denotes a subject whose stromal cells, such as endothelial cells, fibroblasts and/or leukocytes express at the cell surface and/or secrete TNFα protein, as evaluated by flow cytometry, immunohistochemistry or ELISA.

According to the invention, the melanoma can be a genetic melanoma (or familial melanoma) or melanoma caused by UV radiation.

In one embodiment, the melanoma is caused by one or several mutations in the B-Raf gene (like the V600E mutation).

In a particular embodiment, the TNFα blocking agent may be used for the prevention of the relapse of melanoma.

The term "TNFα" or "TNF-alpha" denotes the tumor necrosis factor-alpha. The human TNF-alpha is a human cytokine encoded by the TNF-alpha gene. TNF-alpha, a naturally occurring cytokine, plays a central role in the inflammatory response and in immune injury. It is formed by the cleavage of a precursor transmembrane protein, forming soluble molecules, which aggregate to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

The term "TNFα blocking agent" or "TBA" refers to a molecule, such as protein, antibody, or small molecule that can significantly reduce TNFα properties. Such blocking agents include anti-TNFα antibodies, e.g. infliximab, adalimumab, CDP571 or D2E7, certolizumab and golimumab. Recombinant TNF-receptor based proteins have also been developed (e.g. etanercept, a recombinant fusion protein consisting of two extracellular parts of soluble TNFα receptor 2 (p75) joined by the Fc fragment of a human IgG1 molecule). A pegylated soluble TNF type 1 receptor can also be used as a TNF blocking agent. Additionally, thalidomide has been demonstrated to be a potent inhibitor of TNF production. TNFα blocking agents thus further include phosphodiesterase 4 (IV) inhibitor thalidomide analogues and other phosphodiesterase IV inhibitors.

The term "etanercept" or "ETA" denotes the tumor necrosis factor-alpha (TNFα) antagonist used for the treatment of rheumatoid arthritis. The term "etanercept" (ETA, ETN, Enbrel) is a recombinant TNF-receptor IgG-Fc-fusion protein composed of the p75 TNF receptor genetically fused to the Fc domain of IgG1. Etanercept neutralizes the proinflammatory cytokine tumor necrosis factor-α (TNFα) and lymphotoxin-α (Batycka-Baran et al., 2012).

In one embodiment, the TNFα blocking agent is an anti-TNF-R1 agent or an anti-TNFα agent that is to say an agent which blocks and/or neutralizes the TNFα.

In one embodiment, the TNFα blocking agent is an anti-TNF-R1 agent.

In one embodiment, the TNFα blocking agent is the etanercept.

In the context of the invention, the term "treating" or "treatment", as used herein, means reversing, alleviating, inhibiting the progress of, or preventing the disorder or condition to which such term applies, or one or more symptoms of such a disorder or condition.

As used herein, the term "subject" denotes a mammal, such as a rodent, a feline, a canine, and a primate. Preferably a subject according to the invention is a human.

TNFα blocking agents are well known in the state of art (see for example Konstantinos A. et al, 2000; Marriott J Blake, 1997; Poturoglu S. et al, 2009; Shire Mary G et al., 1998; Wollheim Frank A. 2002).

In one embodiment, said TNFα blocking agent may be a low molecular weight antagonist, e. g. a small organic molecule (natural or not).

The term "small organic molecule" refers to a molecule (natural or not) of a size comparable to those organic molecules generally used in pharmaceuticals. The term excludes biological macromolecules (e. g., proteins, nucleic acids, etc.). Particular small organic molecules range in size up to about 10000 Da, more preferably up to 5000 Da, more preferably up to 2000 Da and most preferably up to about 1000 Da.

In another embodiment, TNFα blocking agent of the invention may be an anti-TNFα or an anti-TNF-R1 antibody which neutralizes TNFα or the receptor TNF-R1 or fragment thereof which neutralizes TNFα or TNF-R1 (see for example Xie J H et Al., 2003).

Antibodies directed against TNFα or TNF-R1 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Antibodies useful in practicing the invention can be polyclonal or monoclonal antibodies. Monoclonal antibodies against TNFα or TNF-R1 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-TNFα or anti-TNF-R1 single chain antibodies. TNFα blocking agent useful in practicing the present invention also include anti-CXCR3 antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to TNFα or TNF-R1.

Humanized anti-TNFα or anti-TNF-R1 antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816, 397).

Then, for this invention, neutralizing antibodies of TNFα or TNF-R1 are selected.

Examples of anti-TNFα antibodies are infliximab (IFX) (a mouse-human chimeric whole antibody) (Remicade™; Centocor, Horsham, Pa., USA), adalimumab (a recombinant human whole antibody) (Humira; Abbott Laboratories, Abbott Park, Ill., USA) and Certolizumab pegol (Cimzia™; UCB, Belgium), which is a PEGylated Fab fragment of a humanized monoclonal antibody that binds and neutralizes human TNFα (see for example Wollheim Frank A. 2002).

In one embodiment, the TNFα blocking agent is the infliximab.

In one embodiment, the antibody according to the invention may be a full human antibody (like the adalimumab).

In still another embodiment, TNFα blocking agent may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then, for this invention, neutralizing aptamers of TNFα or TNF-R1 are selected.

In a particular embodiment, the TNFα blocking agent according to the invention is an inhibitor of TNFα or TNF-R1 expression.

Small inhibitory RNAs (siRNAs) can also function as inhibitors of TNFα or TNF-R1 gene expression for use in the present invention. TNFα or TNF-R1 gene expression can be reduced by contacting a subject or cell with a small double stranded RNA (dsRNA), or a vector or construct causing the production of a small double stranded RNA, such that TNFα or TNF-R1 gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of TNFα or TNF-R1 gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of TNFα or TNF-R1 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of TNFα or TNF-R1 gene expression can be prepared by known methods. These include techniques for chemical synthesis such as, e.g., by solid phase phosphoramadite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing TNFα or TNF-R1. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a particular type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Particular viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Particular viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

In one embodiment, nucleases, endonucleases or meganucleases which target the gene which codes for the TNFα or for the TNF-R1 can be used as TNFα blocking agent.

The term "nuclease" or "endonuclease" means synthetic nucleases consisting of a DNA binding site, a linker, and a cleavage module derived from a restriction endonuclease which are used for gene targeting efforts. The synthetic nucleases according to the invention exhibit increased preference and specificity to bipartite or tripartite DNA target sites comprising DNA binding (i.e. TALE recognition site (s)) and restriction endonuclease target site while cleaving at off-target sites comprising only the restriction endonuclease target site is prevented.

Example of nucleases which may be used in the present invention are disclosed in WO 2010/079430, WO2011072246, WO2013045480, Mussolino C, et al (Curr Opin Biotechnol. 2012 October; 23(5):644-50) and Papaioannou I. et al (Expert Opinion on Biological Therapy, March 2012, Vol. 12, No. 3: 329-342) all of which are herein incorporated by reference.

In order to test the functionality of putative TNFα blocking agent on the treatment and prevention of melanoma, an in vivo test is necessary. For that purpose a syngeneic model of immunocompetent mice orthotopically injected with MHCI expressing melanoma cells (such as B16K1 cells) can be elaborated. MHCI expressing melanoma cells are intradermally injected in wild-type C57BL/6 mice and a TNFα blocking agent is tested for its ability to prevent or cure melanoma.

A further object of the invention relates to a method of treating or preventing melanoma comprising administering to a subject in need thereof a therapeutically effective amount of TNFα blocking agent according to the invention to said subject in whom melanoma cells express MHCI and in whom stroma cells exhibit TNFα expression.

Another object of the invention relates to a method for treating or preventing melanoma in a subject comprising the steps of i) determining the expression level of MHCI in melanoma cells in a sample obtained from the subject and determining the expression level of TNFα in stroma cells in a sample obtained from the subject, ii) comparing the expression levels determined at step i) with predetermined reference values and iii) administering the subject with a therapeutically effective amount of a TNFα blocking agent according to the invention when the levels determined at step i) are higher than their predetermined reference value.

In a particular embodiment, the method may be used for preventing melanoma relapse.

As used herein, the term "sample" denotes for example melanoma sample or a biopsy of the environment of the tumor (cells in contact with the tumor like stroma cells).

Typically, the predetermined reference value is a threshold value or a cut-off value. A "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of the expression level of MHCI and/or TNFα in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of MHCI and/or TNFα in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

PHARMACEUTICAL COMPOSITIONS

A further object of the invention relates to a pharmaceutical composition comprising a TNFα blocking agent according to the invention and pharmaceutically acceptable excipients or carriers.

In one embodiment, the invention relates to a pharmaceutical composition comprising a TNFα blocking agent according to the invention and pharmaceutically acceptable excipients or carriers for use in the treatment and prevention of melanoma in a subject in whom melanoma cells express MHCI and in whom stroma cells exhibit TNFα expression.

In a particular embodiment, the pharmaceutical composition according to the invention may be used for the prevention of the relapse of melanoma.

Any therapeutic agent of the invention as above described may be combined with pharmaceutically acceptable excipients, and optionally sustained-release matrices, such as biodegradable polymers, to form therapeutic compositions. "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of a polypeptide or a nucleic acid according to the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The TNFα blocking agent according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, preferred particular methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

Compositions of the present invention may comprise a further therapeutic active agent. The present invention also relates to a kit comprising a TNFα blocking agent according to the invention and a further therapeutic active agent.

In one embodiment said therapeutic active agent is an anticancer agent. For example, said anticancer agents include but are not limited to vemurafenib, fotemustine, fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, teniposide, campathecins, bleomycin, doxorubicin, idarubicin, daunorubicin, dactinomycin, plicamycin, mitoxantrone, L-asparaginase, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, anthracyclines, MDR inhibitors and Ca2+ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

The invention will be further illustrated by the following figures and examples. However, these examples and figures should not be interpreted in any way as limiting the scope of the present invention.

FIGURES

A, B16F10 and B16K1 cells were incubated with anti-MHCI (H2-K$^b$) and FITC-coupled anti-mouse secondary antibodies (solid line) or secondary antibody alone (dotted line) before analysis by flow cytometry. B and C, 3×10$^5$ B16F10 (A) and B16K1 (B) cells were intra-dermally and bilaterally injected in wild-type and TNF-deficient C57BL/6 mice. Tumor volume was calculated using a calliper at the indicated days. Left panels: data are means±sem of 3 independent experiments and include 7 to 15 mice for each group. Right panels: values determined at the indicated days for each individual tumor are depicted. D, One million B16K1 cells were intra-dermally and bilaterally injected in WT and TNF-deficient C57BL/6 mice, and mice were sacrificed 12 days after. Tumors (n=7-11) were collected and the proportion of the indicated cell populations was determined by flow cytometry. B-D, Bars represent mean values (*: $p<0.05$; : $p<0.01$; *: $p<0.001$).

A, WT mice were injected or not with anti-CD8 antibody and 3 days after, the proportion of circulating CD8 T cells was determined by flow cytometry. B, WT and TNF-deficient mice were injected every 3 days with vehicle or anti-CD8 antibody. Three days after the first injection, 3×10$^5$ B16K1 cells were intra-dermally and bilaterally injected. Tumor volume was calculated using a calliper at the indicated days. Left panels: data are means±sem of 3 independent experiments and include 7 to 8 mice for each group. Right panels: values for individual tumors are indicated. Bars represent mean values (*: $p<0.05$; ***: $p<0.001$).

WT (A and C) and CD8-deficient (B) mice were intraperitoneally injected every 3 days with vehicle or Etanercept (3 mg/Kg). Three days after the first injection, 3×10$^5$ (A and B) or 1 million (C) B16K1 cells were intra-dermally and bilaterally injected. A and B, Tumor volume was calculated using a calliper at the indicated days. Left panels: data are means±sem of 2 independent experiments and include 6 to 7 mice for each group. Right panels: at the indicated days, values for individual tumors are depicted. Bars represent mean values. (*: $p<0.05$; **: $p<0.01$). C, Mice were sacrificed 12 days after B16K1 injection. Tumors (n=5-6) were collected and the proportion of the indicated cell populations was determined by flow cytometry. Values determined for each individual tumor are depicted. Bars represent mean values (*: $p<0.05$).

3×10$^5$ B16K1 cells were intra-dermally and bilaterally injected in wild-type mice. Ten days after, vehicle or Etanercept (3 mg/Kg) was intraperitoneally injected every 3 days. Tumor volume was calculated using a calliper at the indicated days. Left panels: data are means±sem of 2 independent experiments and include 7 to 8 mice for each group. Right panels: at the indicated days, values for each individual tumor are depicted. Bars represent mean values. (*: $p<0.05$).

EXAMPLE

Material & Methods

Reagents and Antibodies:

Final concentrations or dilutions and sources of reagents were as follows: Mouse TNF (1-50 ng/mL) was purchased from Peprotech. Immunohistochemistry on human and mouse melanoma was performed with polyclonal anti-human TNF (Abcam, #ab6671, 1:600), monoclonal anti-human TNF (Abcam, #ab1793, 1:600), MECA79 polyclonal antibody (hybridoma provided by Dr. Girard, IPBS institute, Toulouse, France), anti-mouse CD8 (BD Pharmingen, #550281, 1:100), anti-mouse CD31 (Abcam, #ab28364, 1:100). Secondary antibodies coupled to HRP or fluorophore were from Invitrogen. Flow cytometry analyses were performed using anti-mouse CD45 (eBioscience, #48-0451-80, eFluor450), anti-mouse CD3 (Biolegend, #100312, APC), anti-mouse CD8 (BD Pharmingen, #557959, A700), anti-mouse CD4 (eBioscience, #46-0041-80, PerCP eFluor 710), anti-mouse CD69 (BD Pharmingen, #553236, FITC), anti-mouse MHC-I (mouse Y3 hybridoma), anti-mouse TNF-R1 (Biolegend, #113006, APC), anti-mouse TNF-R2 antibodies (BD Pharmingen, #550086), MHCI dextramers (H-2 K$^b$/SVYDFFVWL, SEQ ID NO:1) (Immudex, 1:100, APC). Isotype controls and dead live reagents for flow cytometry were from BD Pharmingen and Invitrogen, respectively. Etanercept was provided by Dr. Astudillo (CHU, Toulouse, France).

Patients:

Approval of the study was obtained from the scientific review board of the Claudius Regaud Institute (ICR, Toulouse, France). Primary melanoma samples were from patients operated between 2000 and 2012 in the ICR and the CHU Toulouse Purpan.

Immunohistochemistry Analysis in Human Melanoma Samples:

Immunohistochemistry was carried out on 5-μm-thick consecutive sections from paraffin-embedded tumor blocks using a Techmate Horizon slide processor (Dako). Slides were incubated with primary antibodies for 1 hour at room temperature. Antigen-antibody complexes were visualized using a peroxidase-conjugated polymer backbone coupled to a secondary antibody system (EnVision; Dako) and 3,30-diamino-benzidine chromogen (Dako).

Cell Lines:

B16F10 melanoma, LPB fibrosarcoma and Lewis lung carcinoma C57BL/6 cell lines were purchased from ATCC. B16K1 is a genetically modified cell line obtained from B16F10 cells, which stably express MHC Class I molecule H-2Kb. Yumm cells are primary mouse melanoma derived from Braf$^{V600E/+}$, PTEN$^{-/-}$, Cdkn2a$^{-/-}$ C57BL/6 mice. Cells were cultured in DMEM medium containing 10% heat-inactivated fetal calf serum (FCS).

Mice:

TNF-deficient (#5540), TNF-R1-deficient (#2818) and TNF-R2-deficient (#2620) C57BL/6 mice were purchased from Jackson laboratories. WT C57BL/6 mice were from Janvier. CD8 KO mice were a gift from Prof J. Van Meerwijk (Inserm U1043, Toulouse, France). Mice were housed in temperature-controlled rooms in the specific pathogen-free animal facility (Anexplo platform, Toulouse, France), kept on a 12-h light/dark cycle, and had unrestricted access to food and water. All animal studies were conducted according to national and international policies and were approved by the local committee for animal experimentation.

In Vivo Tumorigenesis:

$3 \times 10^5$ B16F10 or B16K1 cells were intra-dermally and bilaterally injected in wild-type, TNF KO, TNF-R1 KO, TNF-R2 KO and CD8 KO C57BL/6 mice. In some experiments, Etanercept (3 mg/Kg) or vehicle (NaCl 0.9%) was intraperitoneally injected every three days before (preventive treatment) or after (curative treatment) B16K1 graft. Tumor volume was calculated using a calliper at the indicated days.

Immune Response Analysis in Mice:

One million B16K1 cells were intra-dermally and bilaterally injected in wild-type, TNF KO or TNF-R1 KO C57BL/6 mice. At day 10-12, mice were sacrificed and draining lymph nodes were collected from each flank, lymph node cells were pooled and counted with a coulter (Beckman Coulter) and incubated with the indicated antibodies and live-dead reagent. Cells were analysed by flow cytometry (BD LSRFortessa), analyses being restricted to viable cells. Alternatively, lymph node cells were re-stimulated with 120 Gy-irradiated B16K1 for 3 days, and cytokines secreted into the culture medium were measured by cytometric bead arrays (BD Cytometric Bead Assay, mouse Th1/Th2/Th17, #560485), according to the manufacturer instructions. Tumors were collected and digested with collagenase D (Roche Diagnostics, #11088866001) for 30 min at 37° C. Cells were stained with the indicated antibodies or MHCI dextramers (APC-conjugated H-2 K$^b$/SVYDFFVWL, SEQ ID NO:1) and live-dead reagents before flow cytometry analysis. Alternatively, tumors were embedded in OCT (Tissus Tek OCT compound, Sakura, #62550-01), frozen under nitrogen and cut using a cryostat. Slides were stained with DAPI and the indicated antibodies for immunohistochemistry and analysed by confocal microscopy (Zeiss, LSM510). At least, two slides per tumor were analysed to determine HEV frequency. CD8+ cells exhibiting lymphoid morphology was quantified in a 100 μm-diameter region around HEV (MECA79+) and non-HEV (CD31+ MECA79−) vessels.

Analysis of Purified CD8 T Cells:

Spleen CD8 T cells were purified from naive wild-type, TNF-R1 KO and TNF-R2 KO mice using mouse CD8 T cell purification kit (Miltenyi Biotec, #130-104-075). CD8 T cells were activated, or not, with anti-CD3 and anti-CD28-coated beads (Life Technologies, #11456D) in the presence of IL-2 (Invitrogen, #PMC0025, 200 U/ml) for 7 to 10 days prior analyses for TNF-R1 and 2 expression by flow cytometry. Fresh and activated CD8 T cells were incubated for 72 h in the presence of recombinant mouse TNF (Peprotek, #315-01A, 1-50 ng/mL). Cell death was evaluated by monitoring plasma membrane permeability increase towards 7-AAD (eBioscience, #00-6993-50, 1:30) by flow cytometry.

Adoptive Transfer in CD8-Deficient Mice:

CD8+ T cells were isolated from WT and TNFR1−/− mice and activated as above described. After 7 days, cell purity and viability averaged 90% for both WT and TNFR1-deficient CD8+ T cells. Three millions of these WT or TNFR1−/− CD8+ T cells were injected into the B16K1 tumors from CD8-deficient mice, which were injected 10 days before with 1 million B16K1 cells. Three days later, animals were sacrificed and the tumor CD8+ T cell content was analysed by flow cytometry.

Statistical Analysis:

Results are expressed as means of at least three independent determinations per experiment. Mean values were compared using Student's t-test (Prism software préciser version). Differences were considered to be statistically significant when P<0.05 (*P<0.05; P<0.01; *P<0.001; n.s.: not significant).

Results

TNF is Abundant in Human Primary Melanoma with Massive CD8 T Cell Infiltration.

Two recent studies indicate that high density of tumor-infiltrating lymphocytes (TILs) is associated with HEV formation in human primary melanoma. We initially evaluated by immunohistochemistry TNF expression in human primary melanoma exhibiting low or high CD8+ TIL content and HEV density. Whereas TNF was minimally, or even not expressed at all, in peritumoral skin region and normal nevi, TNF was expressed at high levels in melanomas exhibiting strong CD8 T cell infiltration and high HEV density (data not shown). As a matter of fact, TNF immunodetection was obvious in melanoma regions exhibiting high lymphocyte infiltration, in which different stromal cell types, including fibroblasts, myeloid cells as well as endothelial cells, were stained with anti-TNF antibodies (data not shown). TNF was also expressed in melanoma cells, which were in close proximity to TILs (data not shown). In sharp contrast, melanoma without TILs as well as non-lymphocyte infiltrated regions from melanoma with TILs displayed no or minimal TNF expression in stromal and melanoma cells (data not shown). Similar observations were made using another anti-TNF antibody (data not shown).

Thus, high TNF expression was associated with lymphocyte melanoma infiltration, which is in good agreement with previous reports showing that inflammatory cytokines are up-regulated in melanoma exhibiting high density of HEVs and CD8+ TILs.

Immunogenic B16 Melanoma Cell Growth is Impaired in TNF-Deficient Mice.

Figure 1:
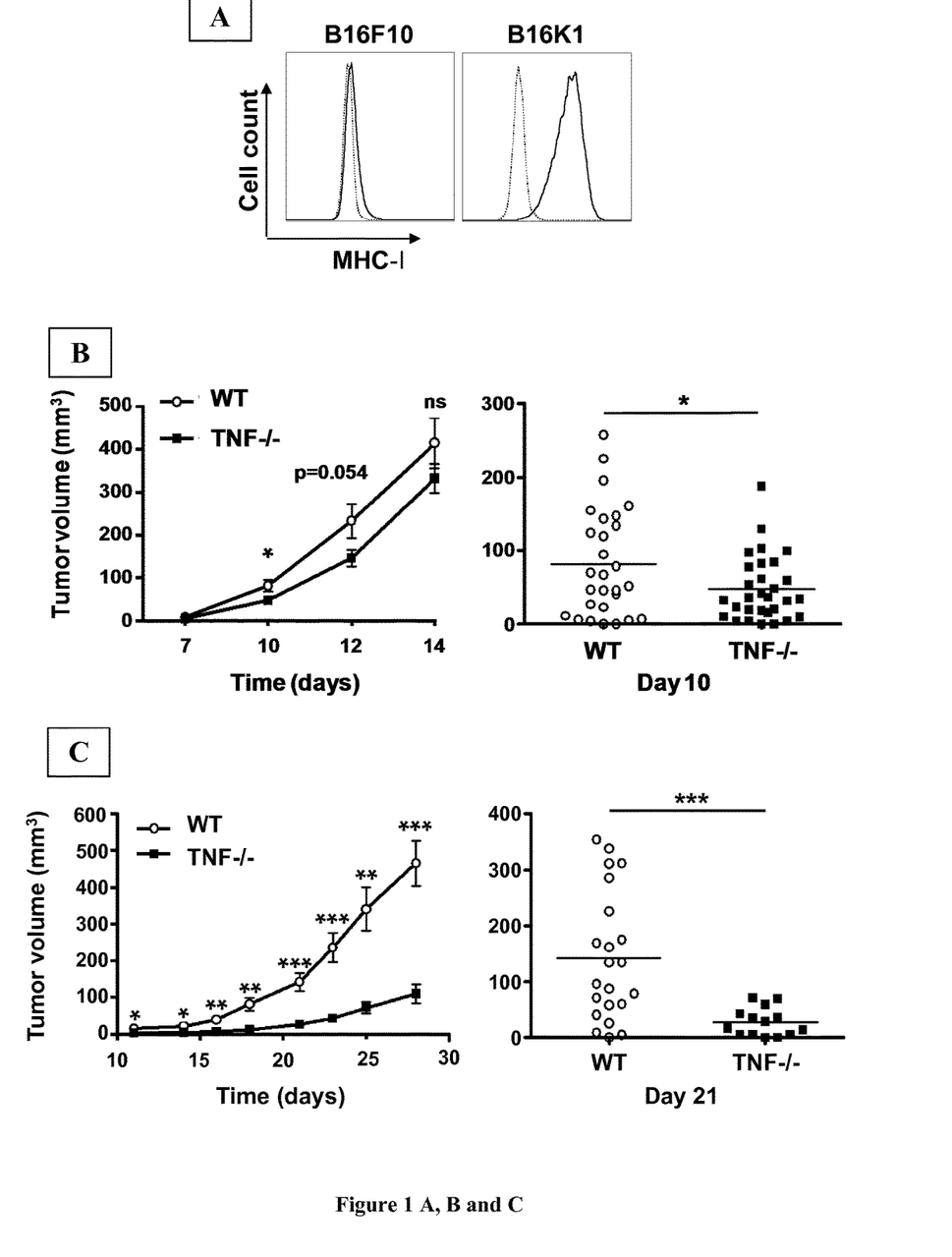
FIG. 1: B16 melanoma growth in wild-type and TNF-deficient mice.

To evaluate whether TNF is instrumental in anti-melanoma CD8+ T cell-dependent immune response, we challenged wild-type (WT) and TNF-deficient mice with orthotopic (i.e., intradermal) injection of B16 mouse melanoma cell lines. We selected B16F10 and B16K1, which constitutively express MHCI at low and high levels, respectively (FIG. 1A). Both B16 melanoma cell lines exhibited similar in vitro cell proliferation rates (data not shown) and expressed TNF-R1, but not TNF-R2 (data not shown). Exogenous TNF did not alter in vitro B16 cell proliferation (data not shown) and growth of spheroids (data not shown). Thus, in agreement with a previous report, it is unlikely that TNF directly exerts a potent pro- or anti-proliferative effect towards B16 melanoma cells. B16F10 cells grew much faster in WT (i.e., immunocompetent) mice than B16K1 cells (FIGS. 1B and 1C), indicating that B16K1 cells are indeed more immunogenic. Whereas the in vivo tumor growth of B16F10 was minimally reduced in TNF−/− mice (FIG. 1B), that of B16K1 was dramatically impaired at all times (FIG. 1C).

The role of host TNF receptors was next evaluated by comparing B16 tumor growth in WT and TNF-R1−/− or TNF-R2−/− mice (data not shown). Whereas B16F10 grew similarly in WT and in either TNF-R-deficient mice (data not shown), B16K1 tumor growth was significantly reduced in TNF-R1−/− mice, but not in TNF-R2−/− mice (data not shown). Thus, our data indicate that host TNF plays a major host TNF-R1-dependent tumor-promoting role in the development of immunogenic mouse melanoma (i.e., expressing MHCI at high levels).

The contribution of host TNF to tumor growth was next evaluated using two additional melanoma cell lines. B16-BL6 (MHCI$^{low}$) tumor growth was not significantly impaired in TNF−/− mice (data not shown). In sharp contrast, BrafV600E/+, Pten−/−, Cdkn2a−/− C57BL/6 primary mouse melanoma cells (Yumm cells), which constitutively expressed MHCI at high levels, displayed significant tumor growth reduction in TNF−/− mice (data not shown). The role of host TNF in tumorigenesis was also assessed towards LPB fibrosarcoma and Lewis lung carcinoma, which spontaneously expressed MHCI at high and low levels, respectively (data not shown). Whereas LPB fibrosarcoma tumor growth was severely impaired in TNF-deficient mice at all times, that of Lewis lung carcinoma was minimally affected (data not shown).

Collectively, our data indicate that MHCI expression level at the cell surface of tumor cells is correlated with the extent of growth inhibition induced by TNF deficiency.

CD8 T Cell-Dependent Immune Response and Tumor Infiltration is Enhanced in TNF-Deficient Mice.

The consequences of host TNF deficiency on the immune response were next investigated. To this end, WT and TNF-deficient mice were orthotopically injected with 1 million of B16K1 cells and sacrificed 12 days later. Under our experimental protocol, B16K1 tumor weights were significantly reduced in TNF-deficient mice (data not shown), further confirming the tumor-promoting role of host TNF towards immunogenic mouse melanoma. The absolute numbers of CD45+ leukocytes as well as CD4+ and CD8+ T cells were significantly increased in draining lymph nodes of TNF-deficient mice (data not shown). Analysis of CD69, a T cell activation marker, indicated that the number of activated CD4 and CD8 T cell was greater in TNF-deficient mice (data not shown). Upon restimulation of lymph node cells with irradiated B16K1 cells, the production of IFNγ, IL-6 and IL-10 was enhanced by TNF deficiency (data not shown). Of note, IL-17 and IL-4 were not detected under our experimental conditions.

Figure 1D:
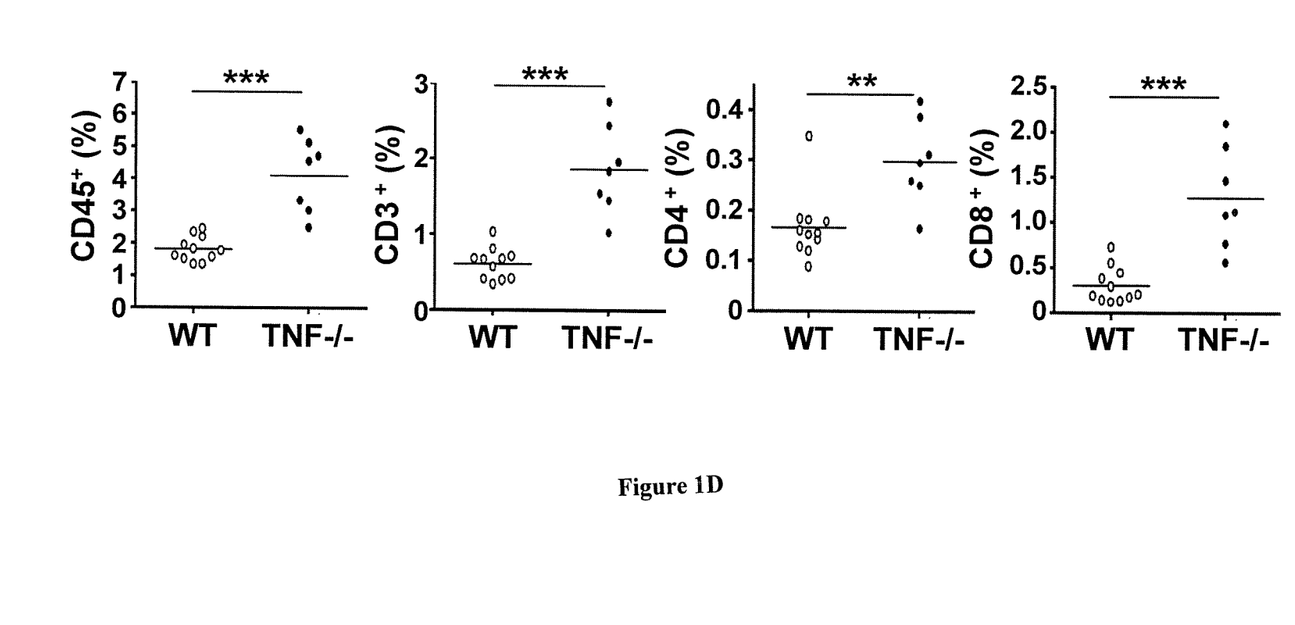

Analysis of leukocyte tumor content by flow cytometry indicated a major increase of CD45+ and CD3+ cell tumor infiltration in TNF-deficient mice as compared to WT mice (FIG. 1D). In addition, the proportion of leukocyte content was altered in tumors derived from TNF-deficient mice, with a significant increase of CD4+ and CD8+ T cells (FIG. 1D), including Treg (CD4+ Foxp3+) and B16 melanoma-specific CD8+ T cells, as evaluated by dextramer technology (data not shown). Of note, the ratio of CD8+ T cells to CD4+ T cells was significantly higher in tumors from TNF-deficient mice (data not shown). Moreover, the proportion of intratumor MDSC (Gr1+CD11b+) was not affected by TNF deficiency (data not shown).

Recent studies indicated that HEV density is directly correlated to CD8 T cell infiltration in human and mouse tumors, including melanomas (32-36). We sought to evaluate by immunohistochemistry whether CD8 T cell infiltration was associated with HEV differentiation in B16 mouse tumors developed in WT and TNF-deficient mice (data not shown). Twelve days after B16K1 cell intradermal injection, whereas only 20% of tumors from WT mice displayed HEVs (denoted as MECA-79+ vessels), 65% of tumors from TNF-deficient mice were positive for HEV (data not shown). We next quantified the number of CD8 T cells (CD8+ cells with lymphoid morphological features) that surrounded HEV (CD31+ MECA79+) and non-HEV (CD31+ MECA79−) vessels (data not shown). In both WT and TNF-deficient mice, the CD8 T cell number was higher next to HEV vessels than around MECA79− CD31+ vessels (data not shown). This data indicates that HEVs are functional and represent a major gateway for CD8 T cell tumor infiltration in melanoma, regardless TNF expression in stromal cells. Moreover, the density of CD8 T cells was higher next to non-HEV vessels from TNF−/− mice as compared to their WT counterparts, further arguing that host TNF reduces CD8 T cell melanoma infiltration. Abundant HEV vessels were also found in tumors derived from both TNF-R1−/− and TNF-R2−/− mice (data not shown). As a matter of fact, CD8 T cell density next to HEVs was significantly increased in TNF-R1−/− mice (data not shown), indicating that host TNF impairs CD8 T cell melanoma infiltration mainly in a TNF-R1-dependent manner.

Collectively, our data indicate that TNF is unlikely instrumental in HEV differentiation and CD8 T cell infiltration within melanoma but rather constitutes a negative feedback for both events under our experimental conditions.

CD8+ Tumor-Infiltrating Lymphocyte (TIL) Content is Increased in TNF-R1-Deficient Mice.

The role of host TNF receptors was next evaluated by comparing B16K1 tumor growth in WT and TNF-R1−/− or TNF-R2−/− mice. B16K1 tumor growth was significantly reduced in mice lacking TNF-R1 but not TNF-R2 (data not shown), indicating that the host TNF/TNF-R1 axis promotes the development of immunogenic mouse melanoma. We hypothesized that host TNF-R1-dependent TNF signaling impairs CD8+ T cell-dependent immune response. In accordance with this tenet, CD8+ TIL content was increased in TNF-R1-deficient mice similarly to TNF-deficient mice (data not shown), including TRP2-specific CD8+ T cells (data not shown), as evaluated by using MHC-I dextramer technology. Moreover, abundant HEV vessels surrounded by high CD8 T cell density were frequently found in tumors derived from TNF-R1−/− mice (5 out of 6 tumors exhibited HEVs) (data not shown). Thus, host TNF-R1 reduces the content of both HEVs and CD8+ T cells within melanoma.

TNF Triggers Activated CD8 T Cell Death Mainly in a TNF-R1-Dependent Manner.

We sought to evaluate whether TNF-deficient CD8 T cells displayed intrinsic alterations that may account for the above observations. CD8 T cells from naive WT and TNF-deficient mice were purified, stimulated with anti-CD3 and anti-CD28 coated beads, and proliferation (data not shown) and IFNγ secretion (data not shown) were evaluated. None of those biological responses was altered by TNF deficiency, indicating that TNF-deficient CD8 T cells do not exhibit major intrinsic alterations under our experimental conditions.

Analysis of TNF receptor expression on purified CD8 T cells, indicated that freshly isolated CD8 T cells expressed TNF-R2 but not TNF-R1 (data not shown). Upon polyclonal stimulation, TNF-R2 expression was strongly up-regulated. Moreover, TNF-R1 became significantly expressed on activated CD8 T cell surface (data not shown). Neither cell proliferation nor cell death was affected by TNF-R1 deficiency upon polyclonal activation (data not shown). Seven days post polyclonal activation, TNF-R1-deficient or proficient CD8+ T cells were injected into the B16K1 tumors developed in CD8-deficient mice. Three days later, mice were sacrificed, and CD8+ T cell content was analysed in the tumors. As a matter of fact, TNF-R1 deficiency significantly enhanced the accumulation of live CD8+ T cells into the tumors (data not shown). The latter data suggests that TNF impairs CD8+ TIL content through a direct effect on activated CD8+ T cells in a TNF-R1-dependent manner. One putative underlying mechanism could be the induction of cell death of activated CD8+ T cells. Because this hypothesis is technically difficult to evaluate in vivo, we next examined the in vitro sensitivity of purified CD8+ T cells to exogenous TNF by monitoring 7AAD uptake to analyse plasma membrane permeability (data not shown). Freshly isolated WT CD8 T cells were fully resistant to TNF at all doses. Ten days after polyclonal stimulation, TNF triggered activated wild-type CD8 T cell death (data not shown). Of note, the cytotoxic effect of TNF on activated wild-type CD8 T cells was already detected at concentration as low as 5 ng/mL (data not shown). Moreover, TNF-induced CD8 T cell death was associated with caspase-3 activation, as evaluated by flow cytometry (data not shown). TNF-R1 deficiency and, to a lesser extent, TNF-R2 deficiency impaired exogenous TNF-induced cell death (data not shown) and caspase 3 activation (data not shown) in activated CD8 T cells.

Altogether, these findings indicate that TNF-triggered activated CD8 T cell death, mainly in a TNF-R1-dependent manner, likely contributes to the resolution of CD8 T cell immune response.

The TNF Pro-Tumorigenic Effect Towards B16 Melanoma Growth is Abrogated in CD8-Deficient Mice.

Figure 2:
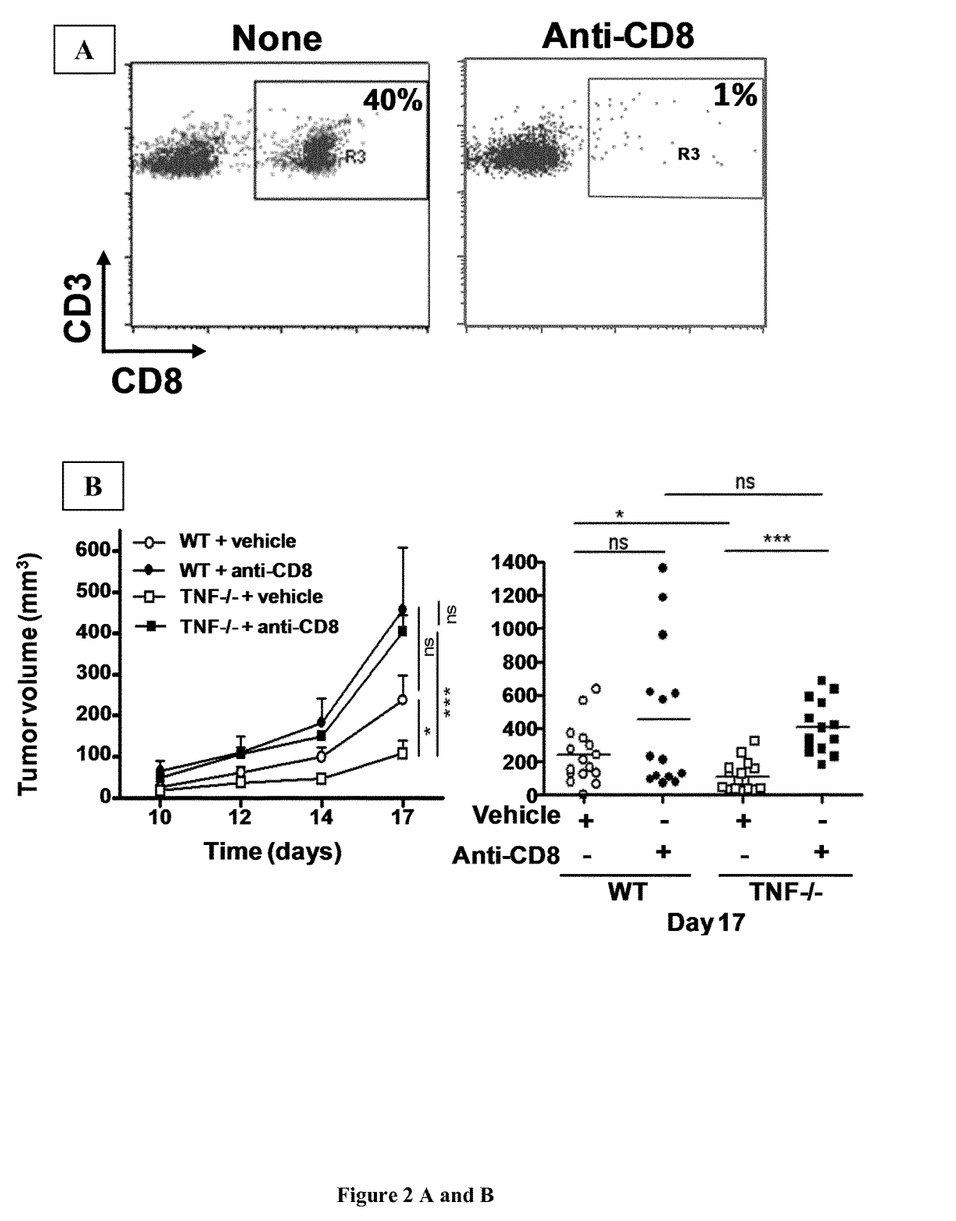
FIG. 2: Impact of CD8 T cell depletion on melanoma growth in wild-type and TNF-deficient mice.

To evaluate whether host TNF deficiency impairs B16 melanoma cell growth by enhancing CD8 T cell tumor infiltration, CD8 T cells were depleted both in WT and TNF-deficient mice (FIG. 2). As a matter of fact, anti-CD8 antibody injection depleted CD8+ T cell efficiently (FIG. 2A) and fully restored B16K1 tumor growth in TNF-deficient mice (FIG. 2B). Of note, B16K1 tumor growth was identical in TNF-deficient and -proficient mice depleted for CD8+ T cells, indicating that host TNF melanoma-promoting effects likely dependent on the modulation of CD8 T cell-dependent immune response.

Figure 3A:
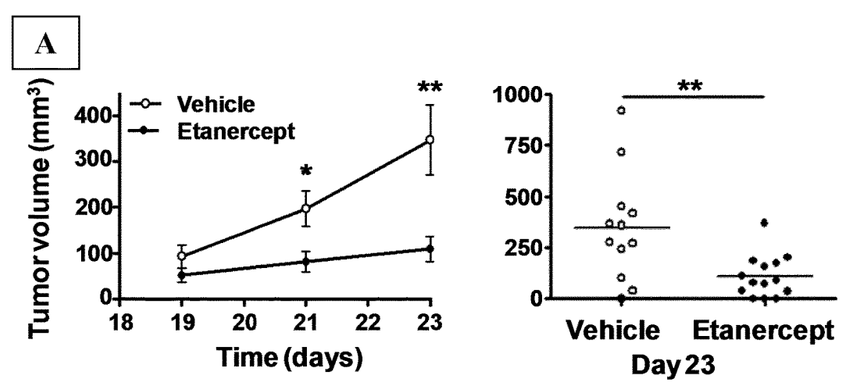
FIG. 3: Impact of pharmacological TNF blockade on melanoma growth in wild-type and CD8-deficient mice.
Figure 3B:
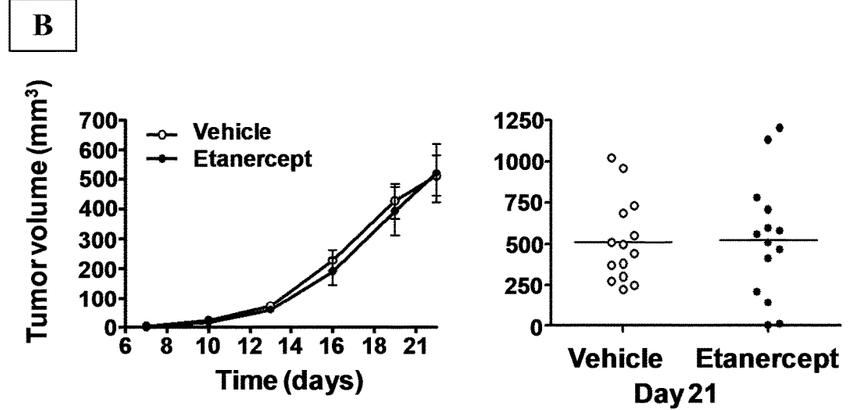
Figure 3C:
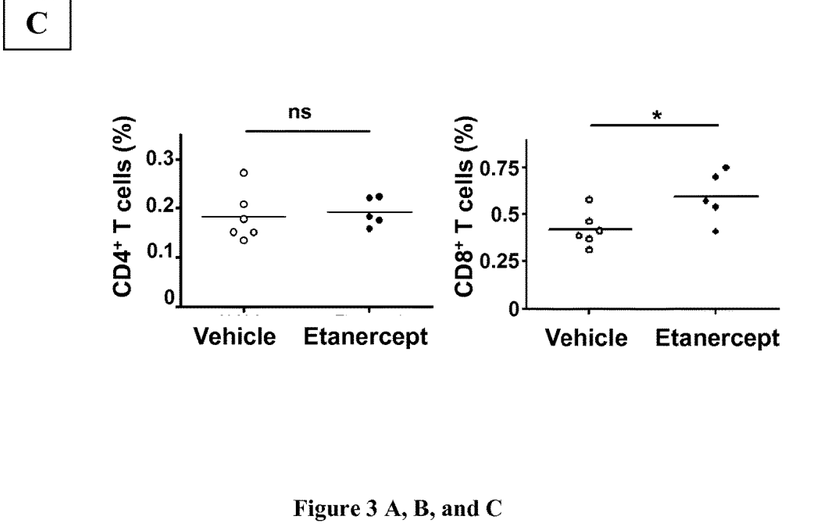

To further investigate the role of TNF in B16 melanoma growth and immune response, wild-type mice were intraperitoneally injected with Etanercept, a soluble human TNF-R2 that efficiently neutralizes mouse TNF. Etanercept was injected 3 days before grafting B16K1 cells and every three days up to 23 days. At all times, Etanercept efficiently neutralized TNF (data not shown) and significantly impaired B16K1 growth in immunocompetent mice (FIG. 3A). In sharp contrast, Etanercept had no effect on B16K1 growth in CD8-deficient mice (FIG. 3B) and in nude mice (data not shown). Accordingly, Etanercept enhanced CD8 T cell-dependent immune response in the lymph nodes (data not shown) and CD8 T cell tumor infiltration (FIG. 3C).

Figure 4:
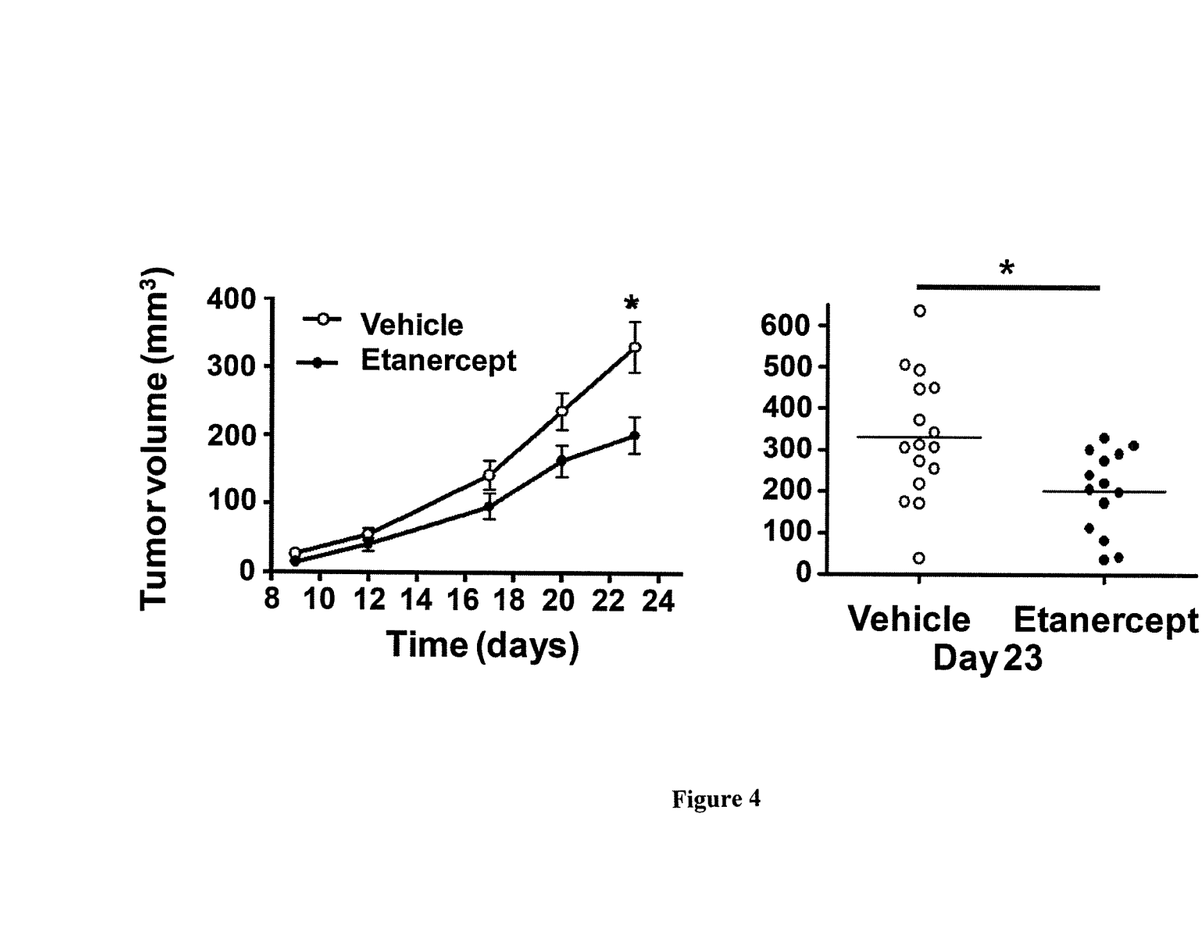
FIG. 4: Etanercept inhibits tumor growth in established melanoma.

We next evaluated whether Etanercept may represent a putative therapeutic agent towards immunogenic melanoma. To this end, we developed a curative protocol by grafting WT mice with B16K1 cells and injecting them 10 days after with Etanercept. Interestingly, Etanercept significantly reduced tumor growth in WT mice having established tumors (FIG. 4), indicating that blocking TNF may be a useful therapeutic strategy to fight against immunogenic melanoma. Of note, a single Etanercept injection triggered both HEV differentiation and infiltration of CD8 T cells in melanoma as evaluated by immunohistochemistry (data not shown).

Collectively, our data demonstrate that the tumor-promoting action of host TNF in B16 melanoma growth is entirely dependent on its ability to impair CD8 T cell activation and tumor infiltration. Blocking TNF enhances CD8+ TIL content and impairs immunogenic melanoma growth in mice.

CONCLUSION

In conclusion, the results of the inventors (see also Bertrand F. et al, in press) allow identifying a new population of patient suffering of melanoma and susceptible to answer positively to a treatment with anti-TNF blocking agent like Etanercept. This population has melanoma cells, which overexpress the MHCI, and stroma cells, which produce TNFα. This is the first time that such population is identified. Blocking TNF or TNF-R1 may enhance CD8+ TIL content and thereby limit melanoma progression in such population.

REFERENCES

Throughout this application, various references describe the state of the art to which this invention pertains. The disclosures of these references are hereby incorporated by reference into the present disclosure.

Balkwill, F. 2009. Tumour necrosis factor and cancer. Nat Rev Cancer 9:361-371.

Batycka-Baran Aleksandra, Michael Flaig, Sonja Molin, Thomas Ruzicka & Joerg C Prinz. Etanercept-induced injection site reactions: potential pathomechanisms and clinical assessment. Expert Opin. Drug Saf. (2012) 11(6).

Bertrand Florie, Julia Rochotte, Céline Colacios, Anne Montfort, Anne Françoise Tilkin-Mariamé, Christian Touriol, Philippe Rochaix, Isabelle Lajoie-Mazenc, Nathalie Andrieu-Abadie, Thierry Levade, Hervé Benoist and Bruno Ségui. Blocking Tumor Necrosis factor α enhances CD8 T cell-dependent immunity in experimental melanoma. Cancer Research in press.

Chopra, M., Riedel, S. S., Biehl, M., Krieger, S., von Krosigk, V., Bauerlein, C. A., Brede, C., Jordan Garrote, A. L., Kraus, S., Schafer, V., et al. 2013. Tumor necrosis factor receptor 2-dependent homeostasis of regulatory T cells as a player in TNF-induced experimental metastasis. Carcinogenesis 34:1296-1303.

Konstantinos A. Papadakis and Stephan R. Targan. Tumor Necrosis Factor: Biology and Therapeutic Inhibitors. Gastroenterology 2000; 119:1148-1157.

Li, B., Vincent, A., Cates, J., Brantley-Sieders, D. M., Polk, D. B., and Young, P. P. 2009. Low levels of tumor necrosis factor alpha increase tumor growth by inducing an endothelial phenotype of monocytes recruited to the tumor site. Cancer Res 69:338-348.

Marriott J Blake. TNF-α antagonists: monoclonal antibodies, soluble receptors, thalidomide and other novel approaches. Exp. Opin. Invest. Drugs (1997) 6(8):1105-1108.

Martinet, L., Le Guellec, S., Filleron, T., Lamant, L., Meyer, N., Rochaix, P., Garrido, I., and Girard, J. P. 2012. High endothelial venules (HEVs) in human melanoma lesions: Major gateways for tumor-infiltrating lymphocytes. Oncoimmunology 1:829-839.

Menon, D. R., Wels, C., Bonyadi Rad, E., Joshi, S., Knausz, H., Lade-Keller, J., Brandner, J. M., and Schaider, H. 2013. TGF-beta1 and TNF-alpha differentially regulate Twist1 mediated resistance towards BRAF/MEK inhibition in melanoma. Pigment Cell Melanoma Res 26:912-916.

Palmieri G I, Morrone S, Lollini P L, De Giovanni C, Nicoletti G, Nanni P, Frati L, Santoni A. TNF impairs in vivo and in vitro natural killer (NK) susceptibility of B16 melanoma cells. Scand J Immunol. 1992 March; 35(3): 279-87.

Poturoglu Sule, Sabahattin Kaymakoglu, Nuray Gurel Polat, Duygu Ibrisim, Emel Ahishali, Filiz Akyuz, Selim Badur, Kadir Demir & Zeynel Mungan. A new agent for tumour necrosis factor-alpha inhibition. Scandinavian Journal of Clinical & Laboratory Investigation. Vol. 69, No. 6, October 2009, 696-702.

Shire Mary G & George W Muller. TNF-α inhibitors and rheumatoid arthritis. Exp. Opin. Ther. Patents (1998) 8(5):531-544.

Smith Michael P., Berta Sanchez-Laorden, Kate O'Brien, Holly Brunton, Jennifer Ferguson, Helen Young, Nathalie Dhomen, Keith T. Flaherty, Dennie T. Frederick, Zachary A. Cooper, Jennifer A. Wargo, Richard Marais and Claudia Wellbrock. The Immune Microenvironment Confers Resistance to MAPK Pathway Inhibitors through Macrophage-Derived TNFα. Cancer Discovery Oct. 2014 4; 1214.

Wilmott J S1, Haydu L E, Menzies A M, Lum T, Hyman J, Thompson J F, Hersey P, Kefford R F, Scolyer R A, Long G V. Dynamics of chemokine, cytokine, and growth factor serum levels in BRAF-mutant melanoma patients during BRAF inhibitor treatment. J Immunol. 2014 Mar. 1; 192(5):2505-13. doi: 10.4049/jimmunol.1302616. Epub 2014 Jan. 31.

Wollheim Frank A. TNF inhibition as therapy for rheumatoid arthritis. Exp. Opin. Investig (2002) 11(7):947-953.

The invention claimed is:

1. A method of treating melanoma in a subject in need thereof, comprising
identifying an immunocompetent subject, wherein immunocompetency is determined by finding in a tumor sample from the subject:
CD8$^+$ tumor infiltrating lymphocytes (TIL),
a high endothelial venule (HEV) MECA79+ differentiation or density,
melanoma cells that express Major Histocompatibility Complex Class I (MHCI), and
stroma cells in contact with the melanoma cells that express tumor necrosis factor-alpha (TNFα) ;
wherein an expression level of MHCI in melanoma cells in the tumor sample from the subject is higher than a predetermined reference value, and an expression level of TNFα in stroma cells in contact with the melanoma cells in the tumor sample from the subject is higher than a predetermined reference value, and
administering to the subject a therapeutically effective amount of TNFα blocking agent.

2. A method for treating melanoma comprising the steps of
i) determining that CD8$^+$ tumor infiltrating lymphocytes (TIL) and a high endothelial venule (HEV) MECA79+ differentiation or density are present in a melanoma tumor sample obtained from a subject, wherein an expression level of Major Histocompatibility Complex Class I (MHCI) in melanoma cells in the sample obtained from the subject is higher than a predetermined reference value and determining that an expression level of tumor necrosis factor-alpha (TNFα) in stroma cells in contact with the melanoma cells in the sample obtained from the subject is higher than a predetermined reference value,
and
ii) administering to the subject a therapeutically effective amount of a TNFα blocking agent.

3. The method of claim 1, wherein the TNFα blocking agent is etanercept.

4. The method of claim 1, wherein the TNFα blocking agent is a monoclonal antibody.

5. The method of claim 4, wherein the monoclonal antibody is infliximab or adalimumab.

6. The method of claim 1, wherein the TNFα blocking agent is a TNF-R1 antagonist.

7. The method of claim 2, wherein the TNFα blocking agent is etanercept.

8. The method of claim 2, wherein the TNFα blocking agent is a monoclonal antibody.

9. The method of claim 8, wherein the monoclonal antibody is infliximab or adalimumab.

10. The method of claim 2, wherein the TNFα blocking agent is a TNF-R1 antagonist.

11. A method of treating or inhibiting growth or metastasis of melanoma in a subject in whom melanoma cells express Major Histocompatibility Complex Class I (MHCI) and in whom stroma cells exhibit tumor necrosis factor-alpha (TNFα) expression comprising
administering to the subject a therapeutically effective amount of an anti-TNF-R1 agent when CD8$^+$ tumor infiltrating lymphocytes (TIL) and a high endothelial venule (HEV) MECA79+ differentiation or density are present in a melanoma tumor sample obtained from the subject, and
an expression level of MHCI in melanoma cells in a sample from the subject is higher than a predetermined reference value, and
an expression level of TNFα in stroma cells in a sample from the subject is higher than a predetermined reference value.

12. A method for treating melanoma in a subject comprising the steps of
i) identifying a subject having an infiltration of CD8+ TIL in a melanoma tumor having a high endothelial venule (HEV) MECA79+ differentiation or density within the melanoma tumor,
ii) determining an expression level of Major Histocompatibility Complex Class I (MHCI) in melanoma cells in a sample obtained from the subject and determining an expression level of tumor necrosis factor-alpha (TNFα) in stroma cells in a sample obtained from the subject,
iii) comparing expression levels determined at step ii) with predetermined reference values and
iv) administering to the subject a therapeutically effective amount of an anti-TNF-R1 agent when the expression levels determined at step ii) are higher than the predetermined reference value.

* * * * *